US010556245B2

(12) United States Patent
Tabata et al.

(10) Patent No.: US 10,556,245 B2
(45) Date of Patent: Feb. 11, 2020

(54) SPRAYING APPARATUS

(71) Applicant: Panasonic Intellectual Property Management Co., Ltd., Osaka (JP)

(72) Inventors: Daisuke Tabata, Osaka (JP); Akira Isomi, Osaka (JP); Yuki Ueda, Osaka (JP)

(73) Assignee: PANASONIC INTELLECTUAL PROPERTY MANAGEMENT CO., LTD., Osaka (JP)

( * ) Notice: Subject to any disclaimer, the term of this patent is extended or adjusted under 35 U.S.C. 154(b) by 49 days.

(21) Appl. No.: 15/958,840

(22) Filed: Apr. 20, 2018

(65) Prior Publication Data

US 2019/0015854 A1    Jan. 17, 2019

(30) Foreign Application Priority Data

Jul. 12, 2017    (JP) .................. 2017-136269

(51) Int. Cl.
  *B05B 7/04*  (2006.01)
  *B05B 1/34*  (2006.01)
  (Continued)

(52) U.S. Cl.
  CPC .............. *B05B 7/0416* (2013.01); *B01D 1/20* (2013.01); *B05B 1/34* (2013.01); *B05B 1/3436* (2013.01);
  (Continued)

(58) Field of Classification Search
  CPC ....... B05B 7/0416; B05B 1/34; B05B 1/3436; B05B 7/0458; B05B 7/0475; B05B 7/066;
  (Continued)

(56) References Cited

U.S. PATENT DOCUMENTS 3,106,346 A * 10/1963 Thomas ............... B05B 7/0433
                                                        239/373
4,006,861 A *  2/1977 Alger ..................... B05B 7/24
                                                        239/373
(Continued)

FOREIGN PATENT DOCUMENTS

JP        8-278047    10/1996
JP     2007-513745     5/2007
(Continued)

OTHER PUBLICATIONS

Extended European Search Report dated Oct. 17, 2018 in related European Patent Application No. 18164878.3.

*Primary Examiner* — Steven J Ganey
(74) *Attorney, Agent, or Firm* — Wenderoth, Lind & Ponack, L.L.P.

(57) ABSTRACT

A spraying apparatus is configured such that a liquid stored in a liquid storage tank is pressurized by a liquid supplier and is supplied to a mist nozzle, so that a liquid flow is introduced from an upstream of a gas-liquid mixing section and a vicinity of a wall surface of the gas-liquid mixing section into the gas-liquid mixing section on an outer lid side. A pressurized gas is supplied from a gas supplier from a facing surface, so that a gas flow is introduced into the gas-liquid mixing section and collides with the liquid flow, and a gas-liquid mixed flow is advanced to a spout portion while circulating the wall surface of the gas-liquid mixing section on the outer lid side.

8 Claims, 9 Drawing Sheets

(51) Int. Cl.
  *B05B 7/10* (2006.01)
  *B01D 1/20* (2006.01)
  *B05B 7/06* (2006.01)
  *B05B 7/24* (2006.01)
  *A61L 9/14* (2006.01)

(52) U.S. Cl.
  CPC .......... *B05B 7/0458* (2013.01); *B05B 7/0475* (2013.01); *B05B 7/066* (2013.01); *B05B 7/10* (2013.01); *B05B 7/2494* (2013.01); *A61L 9/145* (2013.01)

(58) Field of Classification Search
  CPC .......... B05B 7/10; B05B 7/2494; B01D 1/20; A61L 9/145
  USPC .............. 239/302, 373, 337, 398, 422–424.5
  See application file for complete search history.

(56) References Cited

U.S. PATENT DOCUMENTS

| | | | |
|---|---|---|---|
| 5,390,854 A * | 2/1995 | Hench | B05B 7/0458 239/337 |
| 6,352,209 B1 | 3/2002 | Skeath et al. | |
| 8,955,470 B2 | 2/2015 | Kudoh | |
| 2004/0098989 A1 | 5/2004 | Mansour et al. | |
| 2006/0169800 A1 | 8/2006 | Rosell et al. | |
| 2016/0361454 A1 | 12/2016 | Minamio et al. | |

FOREIGN PATENT DOCUMENTS

| | | |
|---|---|---|
| JP | 2011-092889 | 5/2011 |
| JP | 2015-137828 | 7/2015 |
| JP | 2017-000381 | 1/2017 |

\* cited by examiner

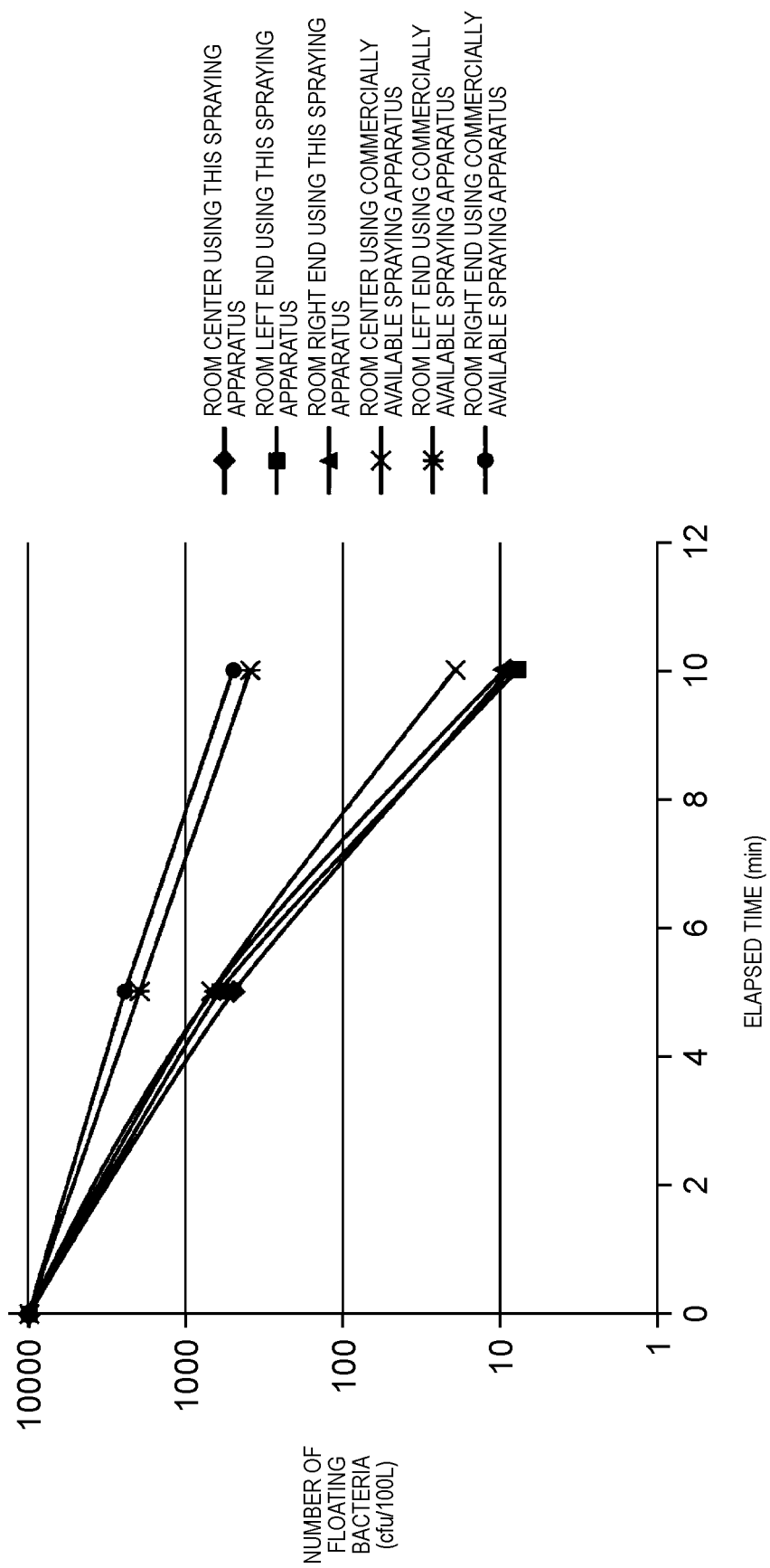

SPRAYING APPARATUS

BACKGROUND

1. Technical Field

The present disclosure relates to a spraying apparatus using a two-fluid nozzle which atomizes a liquid using a gas.

2. Description of the Related Art

In the related art, a spraying apparatus is widely used in a space/material cooling apparatus, a humidifying apparatus, a chemical solution dispensing apparatus, a combustion apparatus, a dust control apparatus, a disinfection apparatus by spraying disinfecting solution, or the like. The spraying apparatus can be broadly divided into a spraying apparatus using a single-fluid nozzle and a spraying apparatus having a two-fluid nozzle. The single-fluid nozzle atomizes a liquid by spouting the liquid from a micro aperture. The two-fluid nozzle atomizes a liquid by using a gas such as an air, nitrogen, or steam. In the spraying apparatuses, in general, the spraying apparatus having the two-fluid nozzle is superior to the spraying apparatus having the single-fluid nozzle in atomization performance because the two-fluid nozzle atomizes a liquid using energy of a gas.

As an example of the spraying apparatus using the two-fluid nozzle, for example, there is a spraying apparatus disclosed in Japanese Unexamined Patent Application Publication No. 8-278047. As the spraying apparatus disclosed in Japanese Unexamined Patent Application Publication No. 8-278047, there is mist nozzle 300 illustrated in FIGS. 8A and 8B. In mist nozzle 300, nozzles 301 which are respectively connected to water supply pipe 302 and compressed air supply pipe 303, which are piped to a ceiling, are suspended with required intervals. Water introduction pipe portion 304 provided in nozzle 301 is connected to water supply pipe 302, water is supplied to water storage chamber 305 having a small capacity of 10 to 50 cc, air introduction pipe portion 306 is connected to compressed air supply pipe 303, and compressed air is supplied. As described above, mist nozzle 300 capable of always supplying water and the compressed air by water supply pipe 302 and compressed air supply pipe 303 provides a spraying apparatus that sprays water and the compressed air from each nozzle 301, and atomizes water droplets.

As the spraying apparatus disclosed in Japanese Unexamined Patent Application Publication No. 2015-137828, there is spraying apparatus 400 illustrated in FIG. 9. Spraying apparatus 400 includes a configuration as described below. Pump chamber 401 is provided at a lower portion in vertically elongated case 400a and an upper portion of pump chamber 401 is tank chamber 402 storing a water storage tank so as to be removable. An upper portion of tank chamber 402 is air blowing space 403. Air intake port 404 is provided on a side wall of case 400a facing air blowing space 403 and upper duct 405 protrudes from a center of an upper surface of case 400a surrounding air blowing space 403. Air blowing fan 406 is installed at a communication port with upper duct 405, nozzle 407 is provided, and air blowing port 408 of the nozzle is provided in an upper frame portion of upper duct 405. Air sucked by air blowing fan 406 is blown out from air blowing port 408, water in the water storage tank to be set in tank chamber 402 is supplied to nozzle 407 by pump 409 provided in pump chamber 401, and is sprayed from nozzle 407. Air sucked by air blowing fan 406 is blown out from air blowing port 408 on an outer periphery of nozzle 407.

SUMMARY

An aspect of the disclosure provides the disclosure provides a spraying apparatus including a liquid storage tank that stores a liquid; a mist nozzle that spouts fine mist; a gas supplier that supplies a pressurized gas to the mist nozzle; and a liquid supplier that supplies a pressurized liquid to the mist nozzle, the pressurized liquid being obtained from the liquid stored in the liquid storage tank. The mist nozzle includes a mist nozzle main body that has a liquid passageway through which the pressurized liquid is supplied from the liquid supplier and a gas passageway through which the pressurized gas is supplied from the gas supplier, an inner lid that is disposed at a tip of the mist nozzle main body, covers an opening of the liquid passageway, and has a flat inner end portion, an outer lid that is disposed at the tip of the mist nozzle main body, covers the inner lid, covers an opening of the gas passageway, and has a flat outer end portion facing the inner end portion of the inner lid, a gas-liquid mixing section that is disposed between the inner lid and the outer lid, is formed at a space of a disc-shaped profile between the inner end portion of the inner lid and the outer end portion of the outer lid, and mixes a gas flow flowing through the gas passageway and a liquid flow flowing through the liquid passageway, a liquid inlet that is provided so as to penetrate at least one portion of the inner end portion of the inner lid in a circumferential direction, communicates with the gas-liquid mixing section, and allows a liquid flow flowing through the liquid passageway to enter the gas-liquid mixing section, a gas inlet that is disposed on a side portion of the gas-liquid mixing section between the inner lid and the outer lid so as to communicate with the gas-liquid mixing section, and allows the gas flow flowing through the gas passageway to enter the gas-liquid mixing section toward the liquid flow entering the gas-liquid mixing section from the liquid inlet, and a spout that is provided so as to penetrate the outer end portion of the outer lid, communicates with the gas-liquid mixing section, and spouts a liquid atomized by mixing the gas flow and the liquid flow in the gas-liquid mixing section as the fine mist.

As described above, according to the spraying apparatus of the aspect of the disclosure, it is possible to provide the spraying apparatus which is capable of spraying a liquid vaporizing so quickly without wetting and having a small particle diameter which does not cause metal corrosion or the like due to wetting. Specifically, since mist that is atomized to 10 μm or less can be sprayed, vaporization of the mist is fast, wetting does not occur, and the liquid can be sprayed. Since a small amount of the gas is required to generate the atomized mist by a unique structure of the mist nozzle in the spraying apparatus, a small compressor in size may be used as one specific example of the gas supplier. Therefore, it is possible to provide an independent and portable spraying apparatus without construction. With the spraying apparatus, it is possible to provide a spraying apparatus capable of spraying a liquid, for example, humidifying air or filtering air in a large space such as a nursing facility, a movie theater, a food factory, or a plant factory.

BRIEF DESCRIPTION OF THE DRAWINGS

FIG. 7 is a graph of a comparative experiment result obtained by measuring a temporal change in the number of floating bacteria in a room in a case where the spraying apparatus of the exemplary embodiment of the disclosure is used;

DETAILED DESCRIPTIONS

Prior to describing an exemplary embodiment, problems in the related art will be briefly described.

As described above, mist nozzle 300 of Japanese Unexamined Patent Application Publication No. 8-278047 is suspended to be attached to water supply pipe 302 and compressed air supply pipe 303, and water and the compressed air can always be supplied to mist nozzle 300. However, if water supply pipe 302 and compressed air supply pipe 303 are piped to be suspended to the ceiling, installation construction for them is necessary, and in many cases, piping construction cannot be performed depending on an installation place of the spraying apparatus.

Therefore, there is a demand for a spraying apparatus which can be easily installed without using the pipes, can eject a large amount of mist in a wide range, and can save energy and maintenance cost.

In order to meet such a demand, there is spraying apparatus 400 of Japanese Unexamined Patent Application Publication No. 2015-137828.

However, in spraying apparatus 400 of Japanese Unexamined Patent Application Publication No. 2015-137828, piping construction is not required, but there is a problem that a maximum mist particle diameter is 50 μm. As described above, in a case where the mist particle diameter is large, it takes time to vaporize the sprayed liquid, that is, the particle diameter is large and vaporization is slow. Therefore, wetting occurs and there is a problem that metal corrosion or the like occurs due to wetting.

The disclosure is made to solve the problem of the related art and an object of the disclosure is to provide a spraying apparatus which is capable of spraying a liquid vaporizing so quickly without wetting and having a small particle diameter which does not cause metal corrosion or the like due to wetting by mixing a liquid with a pressurized gas and spraying mist having a small particle diameter from a gas-liquid mixing nozzle.

Hereinafter, a first exemplary embodiment of the disclosure will be described in detail with reference to the drawings.

The spraying apparatus according to the exemplary embodiment of the disclosure relates to a spraying apparatus that atomizes a liquid to be sprayed by using a gas. An example of the gas includes air, nitrogen, oxygen, inert gas, or the like, which can be appropriately selected according to a purpose of use. An example of the liquid include, for example, water, hypochlorous acid, ozone water, a liquid having other sterilizing functions, or the like, which can be appropriately selected according to a purpose of use.

Configuration of Spraying Apparatus of Exemplary Embodiment

Figure 1:
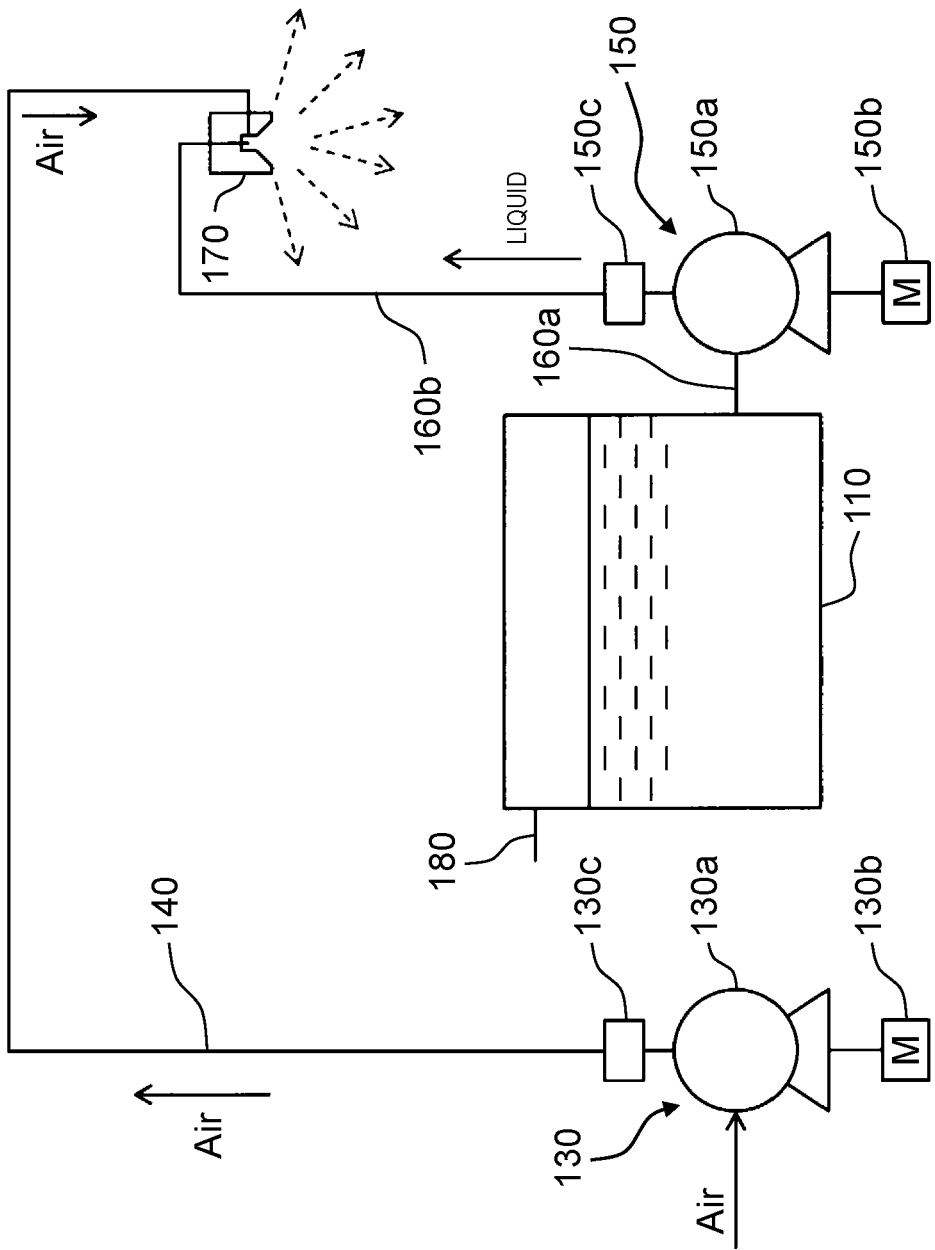
FIG. 1 is a view of a configuration illustrating an example of a spraying apparatus in an exemplary embodiment of the disclosure.

FIG. 1 is a view of a configuration illustrating an example of spraying apparatus 100 in the exemplary embodiment of the disclosure.

Spraying apparatus 100 according to the exemplary embodiment of the disclosure includes water storage tank 110 as an example of a liquid storage tank, liquid pressurizing supplier 150 functioning as an example of a liquid supplier, mist nozzle 170, and gas supplier 130.

Mist nozzle 170 is a nozzle having at least liquid passageway 11 and gas passageway 12 (see FIG. 3A), spraying fine mist by mixing a liquid and a gas, and including a configuration described below in detail.

Water storage tank 110 is a container for storing and holding, for example, a liquid such as water. Water storage tank 110 is configured of a sealed container as an example and is connected to liquid pressurizing supplier 150 by first liquid feeding pipe 160a. Water storage tank 110 is provided with water supply pipe 180 at an upper portion thereof and water such as tap water is supplied from water supply pipe 180 into water storage tank 110 to store and hold water.

Liquid pressurizing supplier 150 is a device or a member for supplying a pressurized liquid to liquid passageway 11 of mist nozzle 170 by using the liquid stored in water storage tank 110. Specifically, liquid pressurizing supplier 150 is connected to water storage tank 110 via first liquid feeding pipe 160a as an upstream side, and is connected to liquid passageway 11 of mist nozzle 170 via second liquid feeding pipe 160b as a downstream side. Liquid pressurizing supplier 150 is configured of, for example, pump 150a for forcibly feeding the liquid supplied from water storage tank 110 to mist nozzle 170, motor 150b for driving pump 150a, flow rate control valve 150c for controlling a flow rate of the liquid forcibly fed from pump 150a, and the like. For example, a discharge pressure or a flow rate of the liquid that is fed from liquid pressurizing supplier 150 to second liquid feeding pipe 160b is controlled by controlling a rotation speed of motor 150b or an opening degree of flow rate control valve 150c.

Gas supplier 130 is a device or a member for supplying a gas such as pressurized air to gas passageway 12 of mist nozzle 170. Gas supplier 130 is connected to gas passageway 12 of mist nozzle 170 via first gas pipe 140 and supplies air from gas supplier 130 to gas passageway 12 of mist nozzle 170. Gas supplier 130 is, for example, configured of compressor 130a, motor 130b for driving compressor 130a, flow rate control valve 130c for controlling a flow rate of a pressurized air that is pressurized by compressor 130a, and the like. The pressurized air that is pressurized by gas supplier 130 is supplied to mist nozzle 170 via first gas pipe 140. For example, a discharge pressure or a flow rate of the pressurized air that is fed from gas supplier 130 to first gas pipe 140 is controlled by controlling a rotation speed of motor 130b or an opening degree of flow rate control valve 130c.

Configuration of Spraying Apparatus of Modification Example

Figure 2:
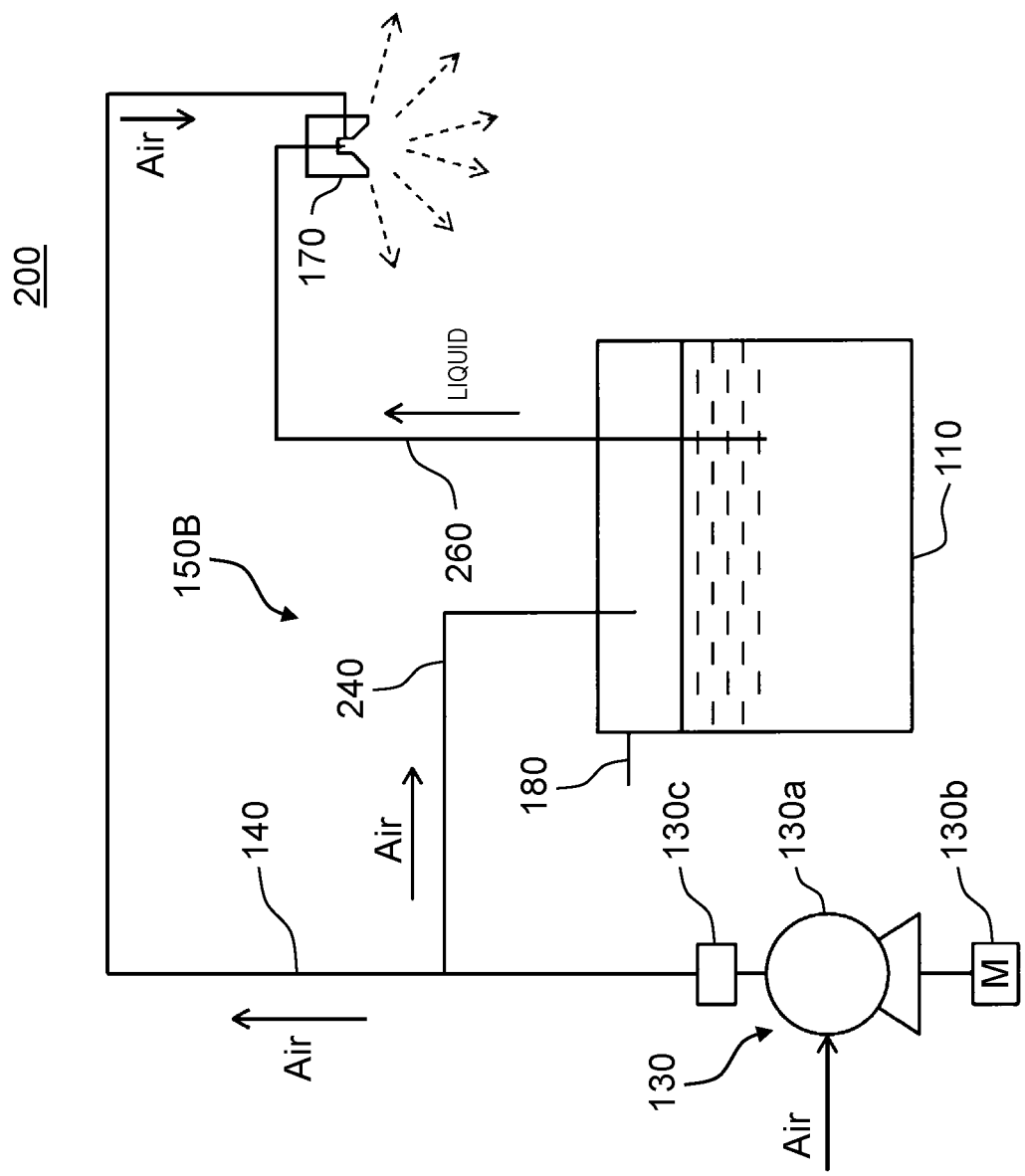
FIG. 2 is a view of a configuration illustrating an example of a spraying apparatus in a modification example of the exemplary embodiment of the disclosure.

FIG. 2 is a view of a configuration illustrating an example of spraying apparatus 200 according to a modification example of the exemplary embodiment of the disclosure.

Spraying apparatus 200 includes water storage tank 110, mist nozzle 170, gas supplier 130, first gas pipe 140, second gas pipe 240 and third liquid feeding pipe 260 functioning as liquid pressurizing supplier 150B.

Mist nozzle 170 is a nozzle for spraying the fine mist, liquid passageway 11 and water storage tank 110 are connected by third liquid feeding pipe 260, and water in water storage tank 110 is capable of being supplied to liquid passageway 11.

Gas supplier 130 and gas passageway 12 of mist nozzle 170 is connected by first gas pipe 140. Second gas pipe 240 branches off from the middle of first gas pipe 140 and is connected to an upper space of water storage tank 110.

Since the configurations of mist nozzle 170 and gas supplier 130 are the same as the configurations of FIG. 1 described above, the detailed description thereof will be omitted.

As illustrated in FIG. 2, first gas pipe 140 branches off between gas supplier 130 and mist nozzle 170, and branched second gas pipe 240 is connected to an upper space of water storage tank 110 to communicate therewith. Therefore, the pressurized air that is pressurized by gas supplier 130 is supplied to the upper space of water storage tank 110 via second gas pipe 240. Since water storage tank 110 has a sealed structure, the liquid in water storage tank 110 is pushed out by the pressurized air entering water storage tank 110 and is supplied to mist nozzle 170 via third liquid feeding pipe 260. Therefore, second gas pipe 240 and third liquid feeding pipe 260 function as liquid pressurizing supplier 150B.

In this case, a configuration is provided such that the liquid is pushed out from water storage tank 110 by using the pressurized air instead of liquid pressurizing supplier 150 such as a pump in the configuration of FIG. 1. Therefore, it is possible to omit the configuration of the pump or the like such as liquid pressurizing supplier 150 and to reduce the equipment cost.

Configuration of Mist Nozzle in Exemplary Embodiment and Modification Example

Figure 3A:
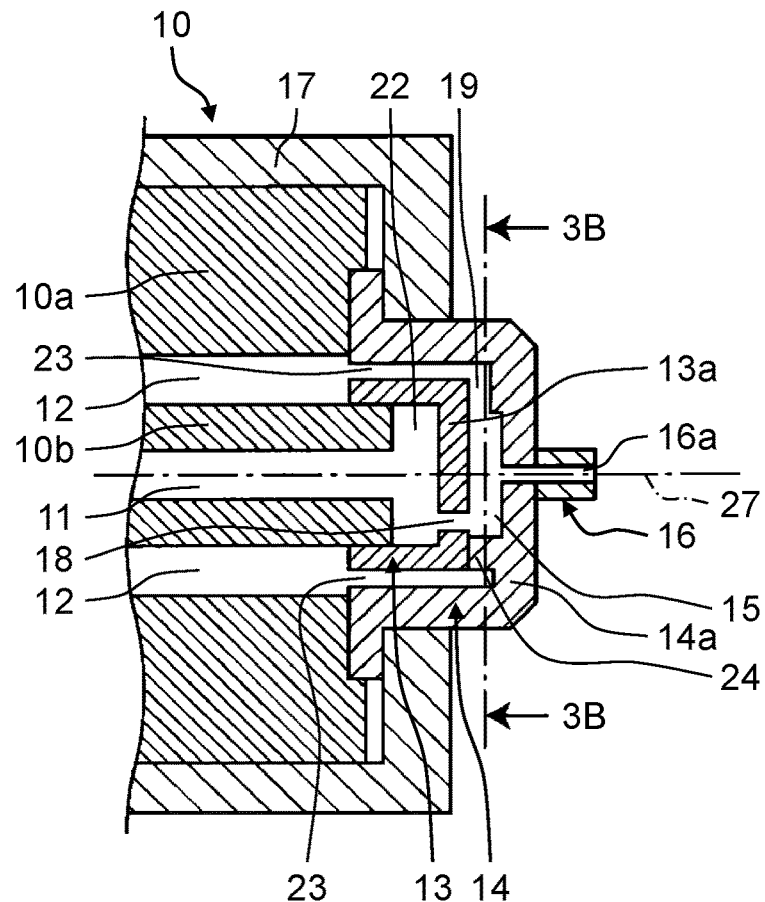
FIG. 3A is a sectional view of a mist nozzle in the exemplary embodiment and the modification example of the disclosure.
Figure 3B:
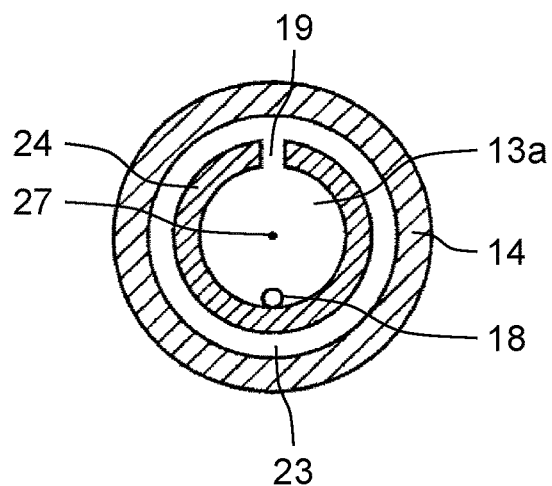
FIG. 3B is a sectional view that is taken along line 3B-3B of FIG. 3A of the mist nozzle in the exemplary embodiment and the modification example of the disclosure.

FIG. 3A is a sectional end view of mist nozzle 10 in the exemplary embodiment and the modification example. Hereinafter, a configuration of mist nozzle 10 will be described with reference to FIG. 3A. FIG. 3B is a sectional view that is taken along line 3B-3B of FIG. 3A.

Mist nozzle 10 includes at least mist nozzle main body 10a, inner lid 13, and outer lid 14. Gas-liquid mixing section 15 is configured of inner lid 13 and outer lid 14. Mist nozzle 10 further includes spraying apparatus lid securing portion 17.

Mist nozzle main body 10a is formed of liquid passageway 11 that is disposed at a center portion of a columnar member along an axial direction and cylindrical gas passageway 12 that is disposed around liquid passageway 11 with intervals along the axial direction respectively. Liquid passageway 11 and gas passageway 12 are partitioned by cylindrical portion 10b positioned at the center portion as a part of mist nozzle main body 10a.

Only a tip side of liquid passageway 11 is illustrated and a liquid supply port (not illustrated) at a rear end is connected to a pump and the like connected to water storage tank 110 as an example of liquid pressurizing supplier 150 or 150B, for example, via second liquid feeding pipe 160b or the water supplying pipe as an example of third liquid feeding pipe 260, or to water storage tank 110 to which second gas pipe 240 is connected. Also only a tip side of gas passageway 12 is illustrated and a gas supply port (not illustrated) at a rear end is connected to an air pressure source configured of an air compressor as an example of gas supplier 130, for example, via first gas pipe 140.

The tip of cylindrical portion 10b slightly protrudes to the tip side from mist nozzle main body 10a except cylindrical portion 10b and inner lid 13 is fixed to the tip thereof.

Inner lid 13 is disposed at the tip of mist nozzle main body 10a, covers an opening of liquid passageway 11, and has a generally C-shaped cross-section having flat inner end portion 13a. First space 22 of a disc-shaped profile is formed between an end surface of cylindrical portion 10b and an inner surface of inner end portion 13a of inner lid 13. Liquid inlet 18 penetrating inner end portion 13a in the axial direction is formed at one portion of an outer peripheral portion of inner end portion 13a of inner lid 13. That is, liquid inlet 18 is positioned at inner end portion 13a of inner lid 13 that is an upstream-side flat surface in a vicinity of an outer peripheral wall surface of gas-liquid mixing section 15, and allows liquid passageway 11 and gas-liquid mixing section 15 to communicate with each other.

Outer lid 14 is disposed at the tip of mist nozzle main body 10a, covers inner lid 13, covers an opening of gas passageway 12, and has a generally Ω-shaped cross-section having flat outer end portion 14a facing inner end portion 13a of inner lid 13. Outer lid 14 is securely sandwiched between the end surface of mist nozzle main body 10a and spraying apparatus lid securing portion 17 so as to cover inner lid 13 with second space 23 having a cylindrical profile with a predetermined interval at a side portion between outer lid 14 and inner lid 13, and cover inner lid 13 while forming gas-liquid mixing section 15 of a space of a disc-shaped profile with a predetermined interval at an end portion between outer lid 14 and inner lid 13. Outer lid 14 may be directly fixed to the end surface of mist nozzle main body 10a without spraying apparatus lid securing portion 17.

In order to reliably form gas-liquid mixing section 15 of the disc-shaped profile with a predetermined interval between outer lid 14 and inner lid 13, annular projection portion 24 is formed on an inner surface of outer end portion 14a of outer lid 14. Therefore, gas-liquid mixing section 15 can be forcedly formed as a space (that is, a gap) of a disc-shaped profile between the inner surface of outer end portion 14a of outer lid 14 and the outer surface of inner end portion 13a of inner lid 13. Annular projection portion 24 may be provided on the outer surface of inner end portion 13a of inner lid 13 instead of being provided on the inner surface of outer end portion 14a of outer lid 14. Gas-liquid mixing section 15 having such a configuration is provided for mixing the gas flow flowing through gas passageway 12 and the liquid flow flowing through liquid passageway 11.

Gas inlet 19 allowing gas passageway 12 and gas-liquid mixing section 15 to communicate with each other is formed at the side portion of gas-liquid mixing section 15 by cutting a part of annular projection portion 24 in a radial direction. Gas inlet 19 is disposed so that an entering direction of the gas flow entering from gas inlet 19 intersects with an entering direction of the liquid flow entering from liquid inlet 18. Gas inlet 19 is located at a position facing liquid inlet 18, which is 180 degrees out of phase with liquid inlet 18 with respect to a center (central axis 27) of mist nozzle main body 10a. The cylindrical portion protrudes to be fixed and to form spout portion 16 having spout 16a penetrating outer end portion 14a and the cylindrical portion in the axial direction at a center of the outer surface of outer end portion 14a of outer lid 14. Spout 16a is disposed on same central axis 27 as liquid passageway 11. On the other hand, liquid inlet 18 is located at a position deviated from central axis 27.

Therefore, gas-liquid mixing section 15 is formed so as to be surrounded by annular projection portion 24, inner lid 13, and outer lid 14, and allows liquid inlet 18 penetrating inner lid 13 along the axial direction, gas inlet 19 formed by cutting annular projection portion 24 along a direction intersecting with the axial direction, and spout 16a penetrating outer lid 14 along the axial direction to communicate with each other.

In such a configuration, the liquid supplied to mist nozzle 10 becomes the liquid flow flowing through liquid passageway 11 from the liquid supply port (not illustrated) on the apparatus tip side with respect to mist nozzle main body 10a, and the liquid flow is supplied to gas-liquid mixing section 15 through first space 22 and liquid inlet 18. Gas supplied to mist nozzle 10 becomes the gas flow flowing through gas passageway 12 from the gas supply port (not illustrated) on the mist nozzle tip side with respect to mist nozzle main body 10a, and the gas flow is supplied to gas-liquid mixing section 15 through second space 23 and gas inlet 19.

When the gas flow and the liquid flow are supplied to gas-liquid mixing section 15, the gas flow and the liquid flow are mixed with each other in gas-liquid mixing section 15, the liquid is atomized, and then the mixed and atomized liquid spouts to an outside from spout 16a of spout portion 16 provided in outer lid 14.

Hereinafter, an atomizing mechanism in gas-liquid mixing section 15 will be described with reference to FIG. 3B. The liquid flow flowing through liquid passageway 11 passes through first space 22 and passes through liquid inlet 18 provided in inner lid 13, and as illustrated in FIG. 3B, the liquid flow is supplied from a vicinity of annular projection portion 24 of gas-liquid mixing section 15 to the direction of spout portion 16.

On the other hand, gas supplied to gas-liquid mixing section 15 through gas inlet 19 located at the position facing liquid inlet 18 with respect to the liquid flow supplied from liquid inlet 18 to gas-liquid mixing section 15 collides with the liquid in gas-liquid mixing section 15. As a result of such a collision, the liquid spreads out to annular projection portion 24 to form a thin film and flow in the circumferential direction of annular projection portion 24, thereby changing from the thin film shape to finer liquid droplets. Furthermore, a gas-liquid mixed flow including the liquid droplets is circulated and aggregated along annular projection portion 24 of gas-liquid mixing section 15. Therefore, the liquid droplets can further be atomized and allow a liquid having a smaller particle diameter to be sprayed from spout 16a.

More specifically, the spraying apparatus includes gas-liquid mixing section 15 having a diameter of 8.0 mm and a height of 2.0 mm, spout 16a of spout portion 16 having a diameter of 1.5 mm and a length of 2.0 mm, liquid inlet 18 having a diameter of 0.7 mm, and rectangular gas inlet 19 having a width of 1.0 mm and a height of 1.0 mm.

The spraying apparatus was supplied with a compressed air, which is an example of the gas, pressurized by 0.2 MPa (gauge pressure) and water, which is an example of the liquid, pressurized by 0.15 MPa (gauge pressure). A Sauter mean particle diameter of the water atomized under the above conditions was evaluated by a laser diffraction technique. A measurement according to the laser diffraction technique was carried out at a position of 300 mm away from the tip of the spraying apparatus and Sauter mean diameter was 10.0 μm.

According to mist nozzle 10 of the configuration described above, in gas-liquid mixing section 15 provided between inner lid 13 and outer lid 14, the liquid entering from liquid inlet 18 and the gas entering from gas inlet 19 collide, circulate, and aggregate along annular projection portion 24, and the liquid is atomized, thereby allowing the atomized liquid to be spout from spout portion 16 as fine mist. As a result, mist nozzle 10, which is capable of spraying a liquid vaporizing so quickly without wetting and having a small particle diameter which does not cause metal corrosion or the like due to wetting, can be provided. More specifically, two-fluid nozzle mist nozzle 10 can be provided which is capable of spraying a liquid having a particle diameter of 10 μm or less as an example of the particle diameter in which evaporation is performed quickly and wetting or the like does not occur.

Figure 4A:
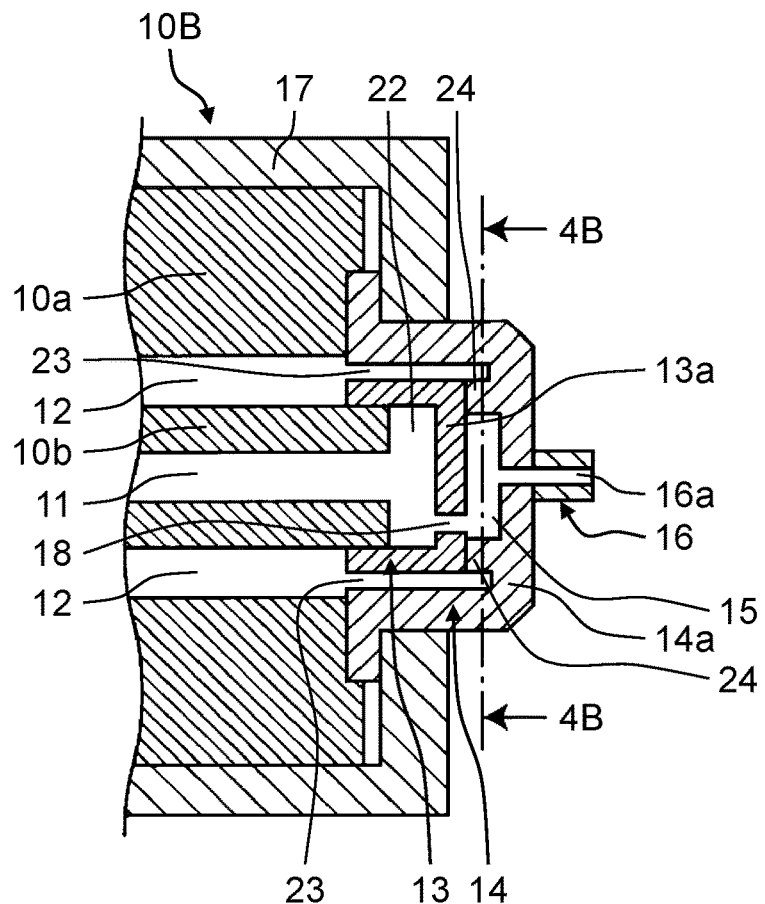
FIG. 4A is a sectional view of a mist nozzle in another modification example of the exemplary embodiment of the disclosure.
Figure 4B:
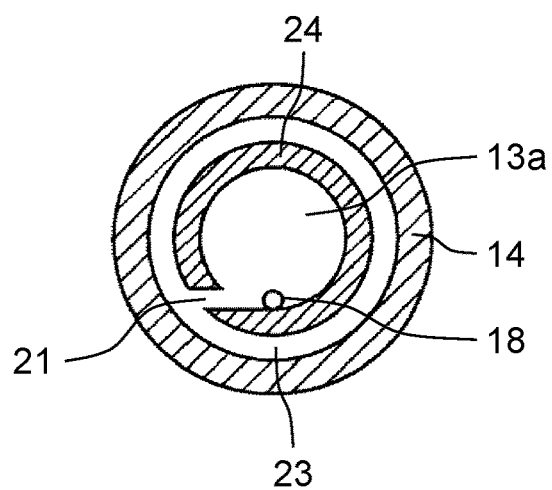
FIG. 4B is a sectional view that is taken along line 4B-4B of FIG. 4A of the mist nozzle in the other modification embodiment of the exemplary embodiment of the disclosure.

Configuration of Mist Nozzle in Another Modification Example of Exemplary Embodiment FIG. 4A is a sectional end view illustrating mist nozzle 10B in another modification example of the exemplary embodiment of the disclosure. FIG. 4B is a sectional view that is taken along line 4B-4B of FIG. 4A. As illustrated in FIGS. 4A and 4B, the liquid flow is supplied from a vicinity of annular projection portion 24 of gas-liquid mixing section 15 toward spout portion 16.

The gas flow is introduced into gas-liquid mixing section 15 from a direction intersecting with the liquid flow to collide with the liquid flow, and the gas-liquid mixed flow is circulated in a circumferential direction of a peripheral wall surface of annular projection portion 24. Therefore, annular projection portion 24 is cut out in a vicinity of liquid inlet 18, in a direction orthogonal to the central axis of liquid inlet 18, and along a tangential direction of the circumferential direction, and is provided with gas inlet 21. In other words, gas inlet 21 is disposed in the vicinity of liquid inlet 18 and is disposed so that an entering direction of the gas flow entering from gas inlet 21 intersects with an entering direction of the liquid flow entering from liquid inlet 18.

The gas flow introduces into gas-liquid mixing section 15 through gas inlet 21 from a direction (for example, the tangential direction of the peripheral wall surface of annular projection portion 24) intersecting with the liquid flow to collide with the liquid flow by such a configuration. Therefore, the liquid spreads out to annular projection portion 24 to become a thin film shape and flows in the circumferential direction of annular projection portion 24, thereby changing from the thin film shape into further fine liquid droplets.

Furthermore, the gas-liquid mixed flow including the liquid droplets is circulated and aggregated along annular projection portion 24 of gas-liquid mixing section 15, and thereby the liquid droplets can be further atomized and a liquid having a smaller particle diameter can be sprayed from spout 16a.

More specifically, the spraying apparatus was supplied with a compressed air, which is an example of the gas, pressurized by 0.2 MPa (gauge pressure) and a water, which is an example of the liquid, pressurized by 0.15 MPa (gauge pressure). Atomization was evaluated under the above conditions. A Sauter mean particle diameter of the water atomized in this state was evaluated by a laser diffraction technique. A measurement according to the laser diffraction technique was carried out at a position of 300 mm away from the tip of the spraying apparatus and Sauter mean particle diameter was 9.6 µm. As a result, there is an effect of agitating the gas-liquid mixed flow and it can be atomized more when liquid inlet 18 and gas inlet 21 are closer to each other than when liquid inlet 18 and gas inlet 19 face each other.

According to the configuration of the other modification example described above, annular projection portion 24 is cut out in the vicinity of liquid inlet 18, in a direction orthogonal to the central axis of liquid inlet 18, and along a tangential direction of the circumferential direction, and is provided with gas inlet 21. Therefore, the gas flow introduces into gas-liquid mixing section 15 through gas inlet 21 from a direction (for example, the tangential direction of the peripheral wall surface of annular projection portion 24) intersecting with the liquid flow to be capable of colliding with the liquid flow. Therefore, the gas-liquid mixed flow can more easily flow in the circumferential direction of annular projection portion 24 to promote circulation and aggregation, the liquid droplets can be further atomized, and the liquid having a smaller particle diameter can be sprayed from spout 16a.

Figure 5A:
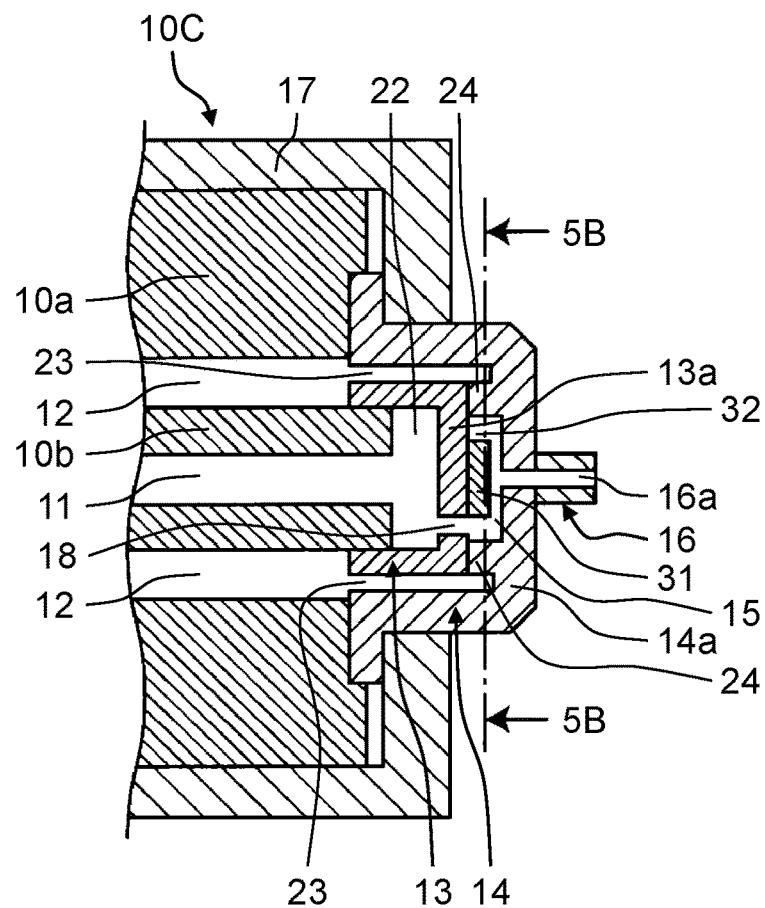
FIG. 5A is a sectional view of a mist nozzle in further another modification example of the exemplary embodiment of the disclosure.
Figure 5B:
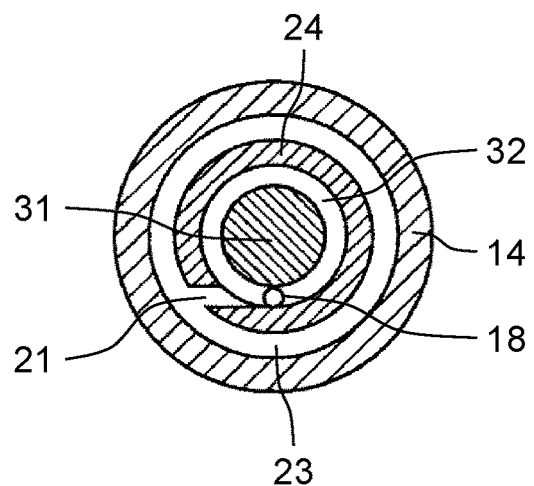
FIG. 5B is a sectional view that is taken along line 5B-5B of FIG. 5A of the mist nozzle in the further other modification embodiment of the exemplary embodiment of the disclosure.

Configuration of Mist Nozzle in Further Another Modification Example of Exemplary Embodiment FIG. 5A is a sectional end view illustrating mist nozzle 10C in further another modification example of the exemplary embodiment of the disclosure. FIG. 5B is a sectional view that is taken along line 5B-5B of FIG. 5A. As illustrated in FIGS. 5A and 5B, in mist nozzle 10C, the liquid flow is supplied from the vicinity of annular projection portion 24 of gas-liquid mixing section 15 to a direction of spout portion 16.

The gas flow is introduced into gas-liquid mixing section 15 from a direction intersecting with the liquid flow to collide with the liquid flow, and the gas-liquid mixed flow is circulated in a circumferential direction of a peripheral wall surface of annular projection portion 24. Therefore, similar to FIG. 4B, annular projection portion 24 is cut out in the vicinity of liquid inlet 18, in a direction orthogonal to the central axis of liquid inlet 18, and along a tangential direction of the circumferential direction, and is provided with gas inlet 21. Furthermore, disc-shaped protrusion portion 31 having a thickness smaller than a height of gas-liquid mixing section 15 is provided on a flat surface on the upstream side that is inner end portion 13a of inner lid 13 of gas-liquid mixing section 15. Therefore, it is possible to form an annular passageway 32 between disc-shaped protrusion portion 31 and annular projection portion 24, a flow of the gas flow and the gas-liquid mixed flow is restricted in the circumferential direction and the flow rate can be increased. In order to restrict the flow of the gas flow and the gas-liquid mixed flow in the circumferential direction to effectively increase the flow rate, a thickness of protrusion portion 31 is set to be at least half the height of gas-liquid mixing section 15.

In order to increase the gas flow, the liquid becomes a thin film shape and flows in the circumferential direction of annular projection portion 24. Furthermore, as described above, it changes from the thin film shape to a more fine liquid droplets by flowing in the circumferential direction of annular projection portion 24 as described above. Furthermore, the gas-liquid mixed flow including the liquid droplets is circulated and aggregated at high speed in the annular passageway 32 between an outer periphery of protrusion portion 31, annular projection portion 24, and outer end portion 14a of outer lid 14 of gas-liquid mixing section 15. Therefore, it is possible to further promote atomization of the liquid and spray the liquid having a smaller predict diameter.

More specifically, a diameter of protrusion portion 31 positioned on a surface on which liquid inlet 18 of gas-liquid mixing section 15 is 1.5 mm, a height thereof is 1.5 mm, and is positioned at a center of gas-liquid mixing section 15.

The spraying apparatus was supplied with a compressed air, which is an example of the gas, pressurized by 0.2 MPa (gauge pressure) and a water, which is an example of the liquid, pressurized by 0.15 MPa (gauge pressure). A Sauter mean particle diameter of the water atomized in the conditions was evaluated by a laser diffraction technique. A measurement according to the laser diffraction technique was carried out at a position of 300 mm away from the tip of the spraying apparatus and Sauter mean particle diameter was 9.1 µm. As a result, the gas-liquid mixed flow between the outer periphery of protrusion portion 31 and outer lid 14 of gas-liquid mixing section 15 can more easily flow in the circumferential direction of annular projection portion 24 to promote circulation and aggregation, and thereby the liquid can be further atomized.

Furthermore, disc-shaped protrusion portion 31 is provided in inner end portion 13a of inner lid 13 of gas-liquid mixing section 15 so that the annular passageway 32 is formed between disc-shaped protrusion portion 31 and annular projection portion 24. As a result, the flow of the gas flow and the gas-liquid mixed flow is restricted in the circumferential direction by the annular passageway 32 so that it is possible to increase the flow rate, to further improve atomization of the liquid, and to spray a liquid having a smaller particle diameter.

EXAMPLES

Figure 6:
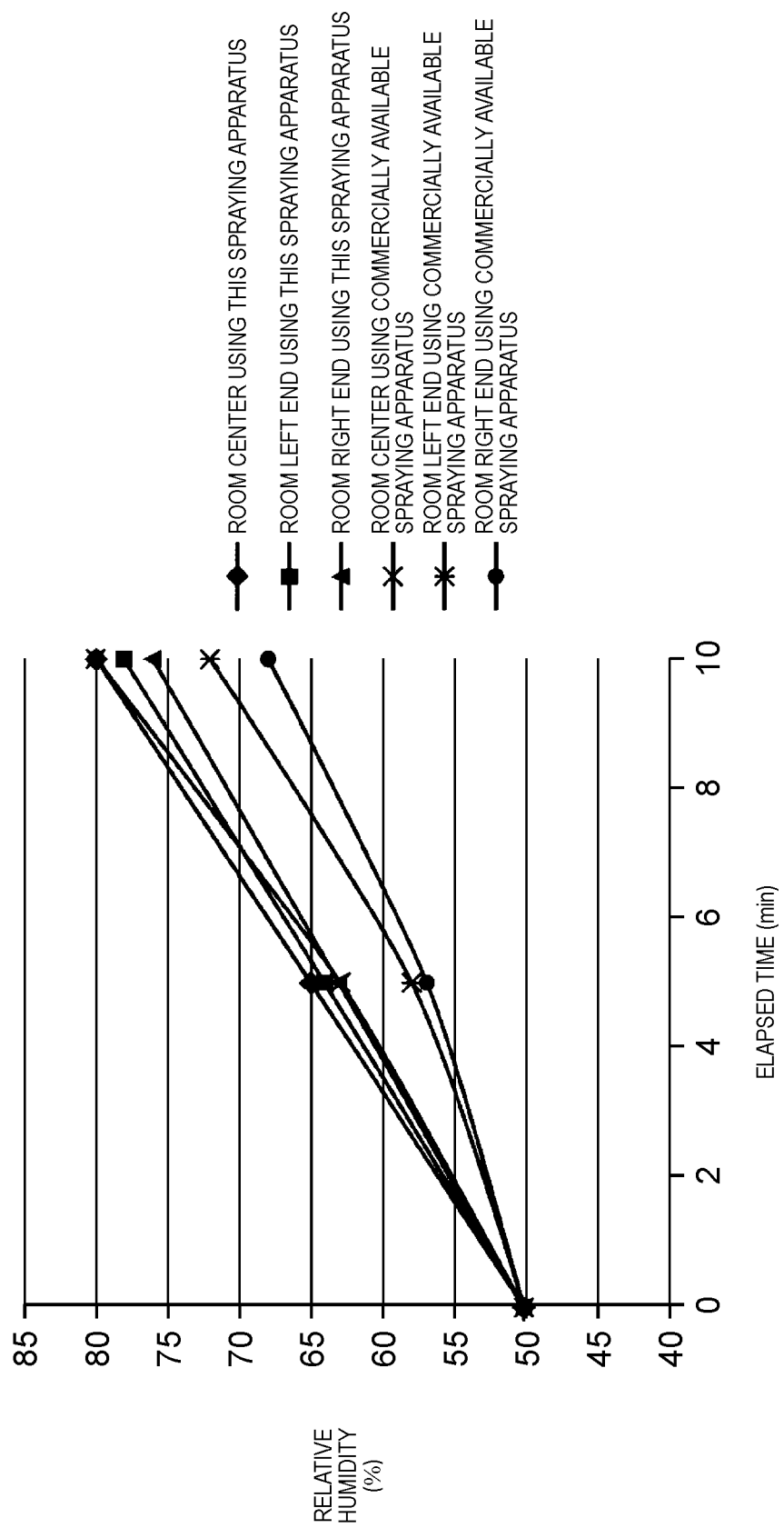
FIG. 6 is a graph of a comparative experiment result obtained by measuring a humidity change in a room in a case where the spraying apparatus of the exemplary embodiment of the disclosure is used.
Figure 8A:
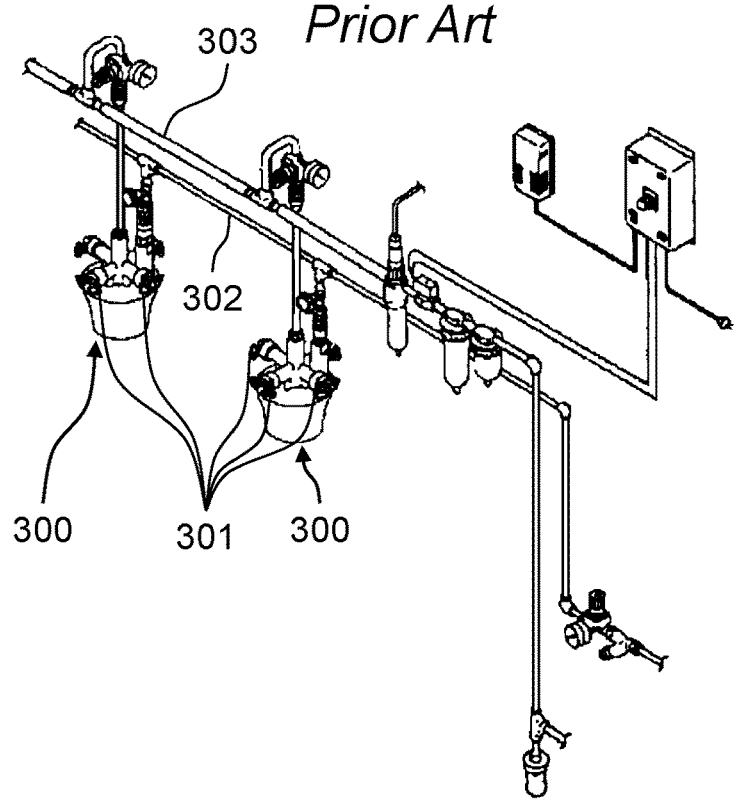
FIG. 8A is a perspective view of a schematic configuration of a spraying apparatus of the related art.
Figure 8B:
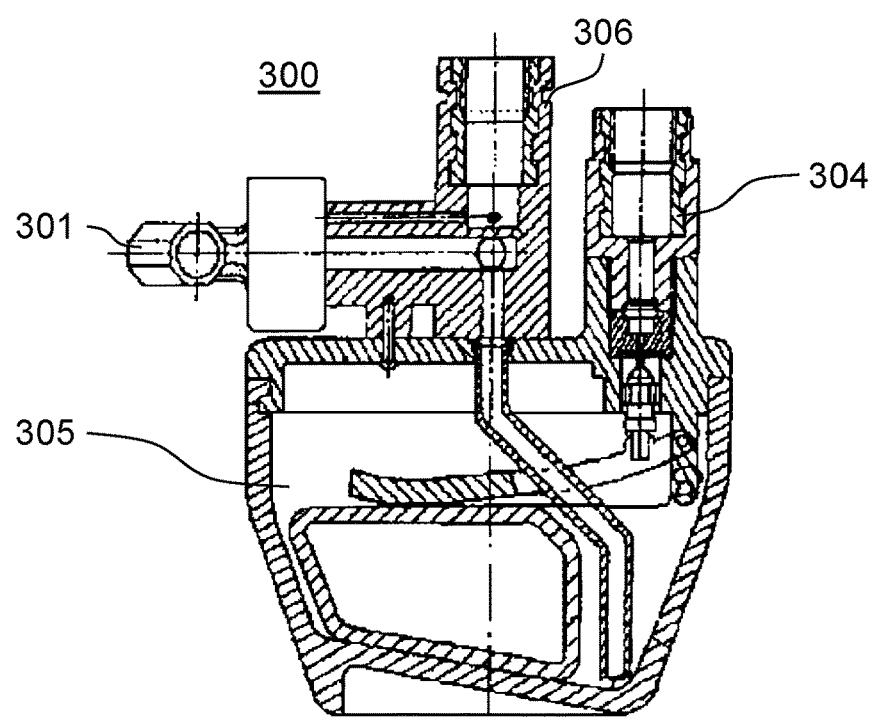
FIG. 8B is an enlarged view of a vertical cross-section of a schematic configuration of the spraying apparatus of the related art.
Figure 9:
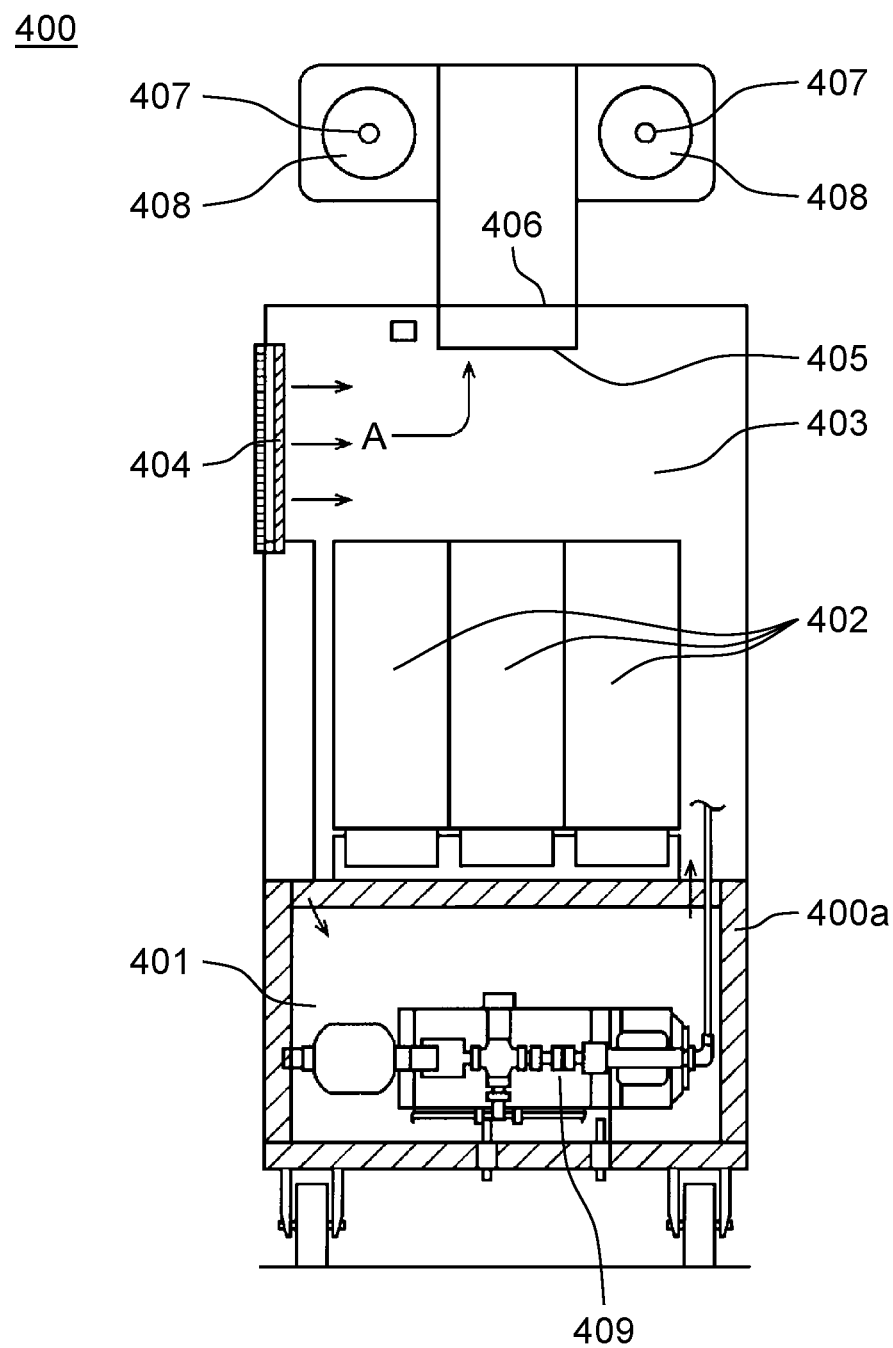
FIG. 9 is a view of a schematic configuration of a spraying apparatus of the related art.

Next, a humidifying effect when using spraying apparatus 100 according to the exemplary embodiment will be described. In a graph of a result of FIG. 6, spraying apparatus 100 is illustrated as "this spraying apparatus". Humidity measurement and confirmation of wetting of a floor or a wall were performed in a state where a size of the room has a width of 5 m, a length of 10 m, a floor area of 50 $m^2$, and a height of 2 m, and ventilation is not performed. Spraying apparatus 100 was disposed at the center of the room and water is sprayed at 50 ml/min. An air pressure supplied to mist nozzle 170 was 0.2 MPa and a water pressure was 0.15 MPa, and in this case, the Sauter mean particle diameter of the mist was 10 μm. The same amount of water was sprayed by using the spraying apparatus in which a commercially available single-fluid nozzle is installed. In this case, the Sauter mean particle diameter of the mist was 50 μm. A change in the humidity in the room is illustrated in FIG. 6. When using mist nozzle 170, as illustrated in FIG. 6, the humidity of the room was changed approximately equally and wetting did not occur on the floor and the wall. This is because vaporization is fast and moisture diffusion is fast due to the fine particle diameter of the mist. On the other hand, in a commercially available spraying apparatus, since an average particle diameter is large, vaporization is slow, and moisture diffusion is slow, humidity distribution in the room increased. Wetting occurred on the floor and the wall in the vicinity of the spraying apparatus.

FIG. 7 illustrates a comparative experiment result obtained by measuring a temporal change in the number of floating bacteria in a room when spraying apparatus 100 is used and a hypochlorous acid solution having a concentration of 200 ppm is sprayed in the same room as that of the humidifying experiment. Also in the graph of the result of FIG. 7, spraying apparatus 100 is illustrated as "this spraying apparatus". An air pressure supplied to mist nozzle 170 was 0.2 MPa and a liquid pressure was 0.15 MPa, and in this case, a liquid spraying amount was 50 ml/min and the Sauter mean particle diameter of the mist was 10 μm. The same amount of the hypochlorous acid solution was sprayed by using the spraying apparatus equipped with a commercially available single-fluid nozzle. In this case, the Sauter mean particle diameter of the mist was 50 μm. As illustrated in FIG. 7, it was found that a disinfection performance of the number of floating bacteria when using spraying apparatus 100 was improved more than a case where the commercially available spraying apparatus. This is because diffusion of hypochlorous acid is also fast due to the fine particle diameter of the mist. Similar to the humidifying experiment, also in the spraying of the hypochlorous acid solution, when using spraying apparatus 100, wetting did not occur on the floor and the wall.

Effects of Exemplary Embodiment and Various Modification Examples

Therefore, according to the exemplary embodiment and the various modification examples, it is possible to spray the mist that is atomized to 10 μm or less. Therefore, vaporization of the mist is fast, wetting does not occur, metal corrosion does not occur due to wetting, and the liquid having a small particle diameter can be sprayed. Since a small amount of the gas is required to generate the atomized mist by a unique structure of mist nozzle 170 in the spraying apparatus, a small compressor in size may be used as gas supplier 130. Therefore, it is possible to provide an independent and portable spraying apparatus without construction. With the spraying apparatus, it is possible to provide a spraying apparatus capable of spraying a liquid, for example, humidifying air or filtering air in a large space such as a nursing facility, a movie theater, a food factory, or a plant factory.

According to the exemplary embodiment and the various modification examples, as an example, the air pressure is 0.2 MPa and the liquid pressure is 0.15 MPa. Therefore, the average particle diameter of the fine mist of the liquid to be sprayed can be 10 μm or less, it is possible to spout the mist having a small particle diameter, and even in a case where the sprayed mist is at the time of a person, it does not wet and does not give the person discomfort. Even in a case where the mist is at the time of metal, since it does not wet, metal corrosion does not occur.

It is possible to achieve the respective effects included in exemplary embodiments by suitably combining any exemplary embodiment or modification example of the above-described various exemplary embodiments or modification examples. Combinations of the exemplary embodiments, combinations of the examples, or combinations of the exemplary embodiments and the examples are possible and combinations of features in different exemplary embodiments or examples are also possible.

The spraying apparatus according to the aspect of the disclosure can provide a spraying apparatus which is capable of spraying a liquid vaporizing so quickly without wetting and having a small particle diameter which does not cause metal corrosion or the like due to wetting. Specifically, the spraying apparatus can be widely used for humidifying air or filtering air in a large space such as a nursing facility, a movie theater, a food factory, or a plant factory by causing the particle diameter of the liquid to be 10 μm or less and using the two-fluid nozzle for spraying the liquid.

What is claimed is:
1. A spraying apparatus comprising:
a liquid storage tank configured to store a liquid;
a mist nozzle configured to spout fine mist;
a gas supplier configured to supply a pressurized gas to the mist nozzle; and
a liquid supplier configured to supply a pressurized liquid to the mist nozzle, the pressurized liquid being obtained from the liquid stored in the liquid storage tank,
wherein the mist nozzle includes:
a mist nozzle main body that has a liquid passageway through which the pressurized liquid is configured to be supplied from the liquid supplier and a gas passageway through which a pressurized gas is configured to be supplied from the gas supplier;
an inner lid that is at a tip of the mist nozzle main body, covers an opening of the liquid passageway, and has a flat inner end portion;
an outer lid that is at the tip of the mist nozzle main body, covers the inner lid, covers an opening of the gas passageway, and has a flat outer end portion facing the flat inner end portion of the inner lid;
a gas-liquid mixing section that is between the inner lid and the outer lid, is defined at a space of a disc-shaped profile between the flat inner end portion of the inner lid and the flat outer end portion of the outer lid, and is configured to mix a gas flow from the gas passageway and a liquid flow from the liquid passageway;
a liquid inlet that penetrates at least one portion of the flat inner end portion of the inner lid in a circumferential direction, is in communication with the gas-liquid mixing section, and is configured to allow the liquid flow from the liquid passageway to enter the gas-liquid mixing section;
a gas inlet that is on a side portion of the gas-liquid mixing section between the inner lid and the outer lid, is in communication with the gas-liquid mixing section, and is configured to allow the gas flow from the gas passageway to enter the gas-liquid mixing section toward the liquid flow from the liquid inlet;
a spout that penetrates the flat outer end portion of the outer lid, is in communication with the gas-liquid mixing section, and is configured to spout, as the fine mist, a liquid atomized by mixing the gas flow and the liquid flow in the gas-liquid mixing section;
an annular projection portion is provided at one of the flat outer end portion of the outer lid and the flat inner end portion of the inner lid; and
the annular projection portion is in contact with the other of the flat outer end portion of the outer lid and the flat inner end portion of the inner lid.
2. The spraying apparatus of claim 1,
wherein the gas-liquid mixing section is defined at the space of the disc-shaped profile between the annular projection portion, the flat outer end portion of the outer lid, and the flat inner end portion of the inner lid, and wherein a part of the annular projection portion is cut to define the gas inlet.

3. The spraying apparatus of claim 2,
wherein the gas inlet faces the liquid inlet with respect to a center of the mist nozzle main body.

4. The spraying apparatus of claim 2,
wherein the gas inlet is configured such that an entering direction of the gas flow from the gas inlet intersects with an entering direction of the liquid flow from the liquid inlet.

5. The spraying apparatus of claim 4, further comprising:
a disc-shaped protrusion portion extending from the flat inner end portion of the inner lid toward the outer lid,
wherein an annular passageway is defined around the disc-shaped protrusion portion in the gas-liquid mixing section.

6. The spraying apparatus of claim 1,
wherein the gas inlet faces the liquid inlet with respect to a center of the mist nozzle main body.

7. The spraying apparatus of claim 1,
wherein the gas inlet is configured such that an entering direction of the gas flow from the gas inlet intersects with an entering direction of the liquid flow from the liquid inlet.

8. The spraying apparatus of claim 7, further comprising:
a disc-shaped protrusion portion extending from the flat inner end portion of the inner lid toward the outer lid,
wherein an annular passageway is defined around the disc-shaped protrusion portion in the gas-liquid mixing section.

* * * * *